United States Patent [19]

Ehmsen et al.

[11] Patent Number: 5,377,668
[45] Date of Patent: Jan. 3, 1995

[54] APPARATUS AND METHOD FOR ENDOSCOPIC DIAGNOSTICS AND THERAPY

[75] Inventors: Ronald J. Ehmsen, Villa Park; Michael H. Ekinaka, Irvine, both of Calif.; Jeffery O. Brown, North Logan, Utah; Mario Cordero, Tustin, Calif.

[73] Assignee: Optimed Technologies, Inc., Orange, Calif.

[21] Appl. No.: 46,409

[22] Filed: Apr. 12, 1993

[51] Int. Cl.⁶ .............................................. A61B 1/00
[52] U.S. Cl. ........................................................ 128/4
[58] Field of Search ............................. 128/4, 7, 6, 20; 606/205, 206, 171, 174

[56] References Cited

U.S. PATENT DOCUMENTS 4,762,120  8/1988  Hussein .................................. 128/6
5,199,417  4/1993  Muller et al. .

Primary Examiner—Richard J. Apley
Assistant Examiner—Beverly A. Meindl
Attorney, Agent, or Firm—Trask, Britt & Rossa

[57] ABSTRACT

A fiberscope is constructed with one or more of a pivoted eyepiece, a cannula insertion assembly capable of housing a retractable fiber bundle and/or delivering distention fluid, a disposable sheath and seal assembly and an encasement for a fiber bundle. The distal end of the encased bundle can be advanced or withdrawn from its protective sheath. When advanced, it may be reoriented in direction by means of linkage to structure which can be manipulated from outside the instrument.

22 Claims, 5 Drawing Sheets

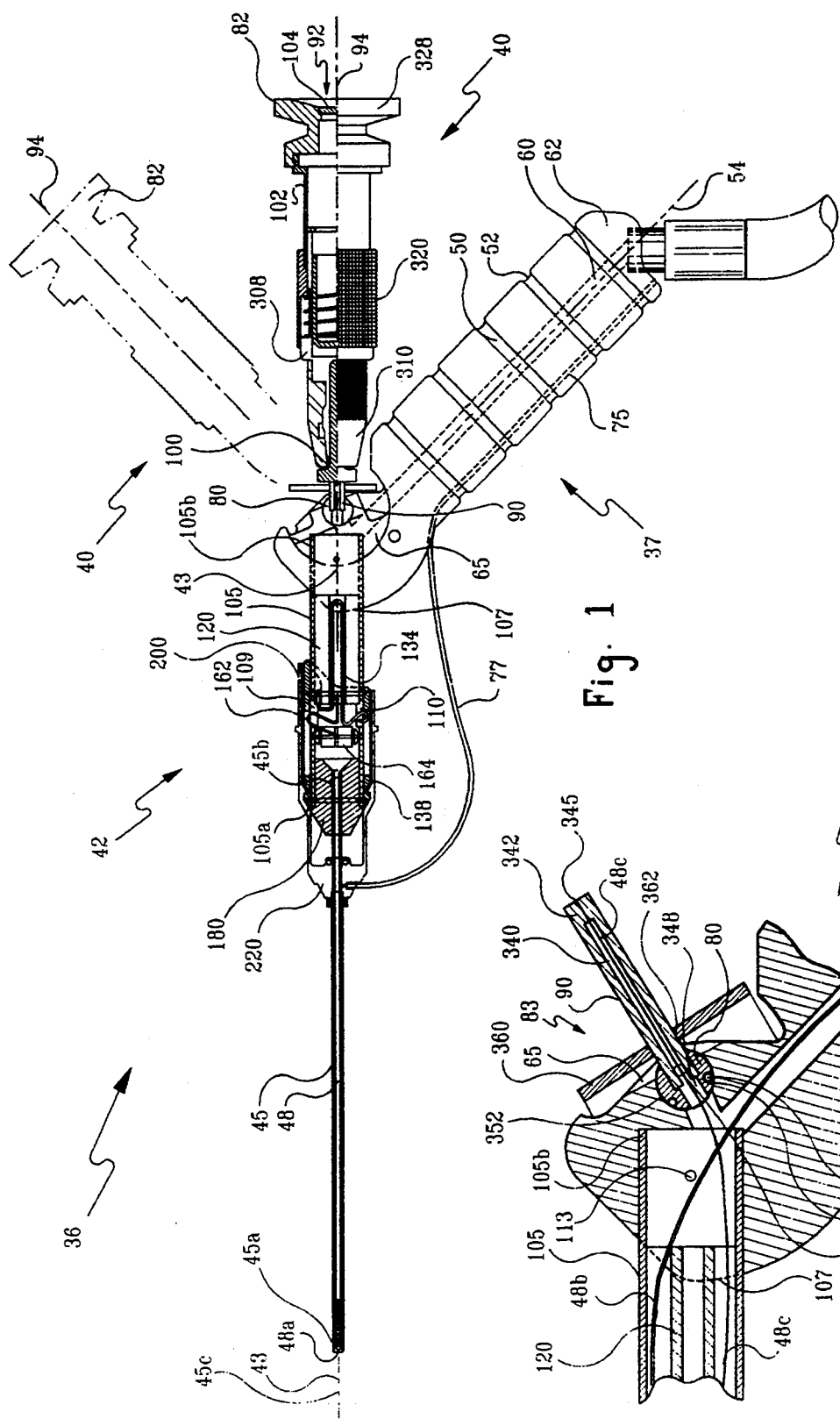

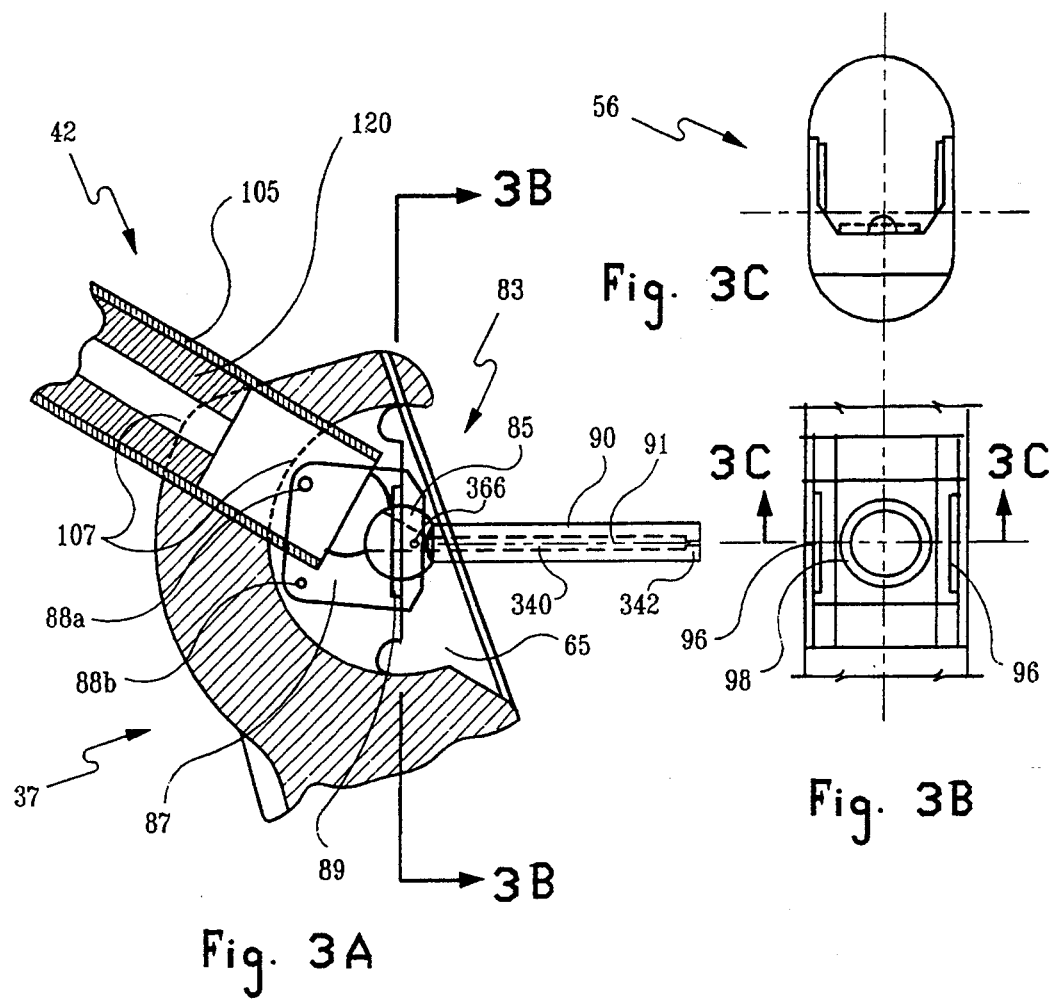
Fig. 3A
Fig. 3B
Fig. 3C
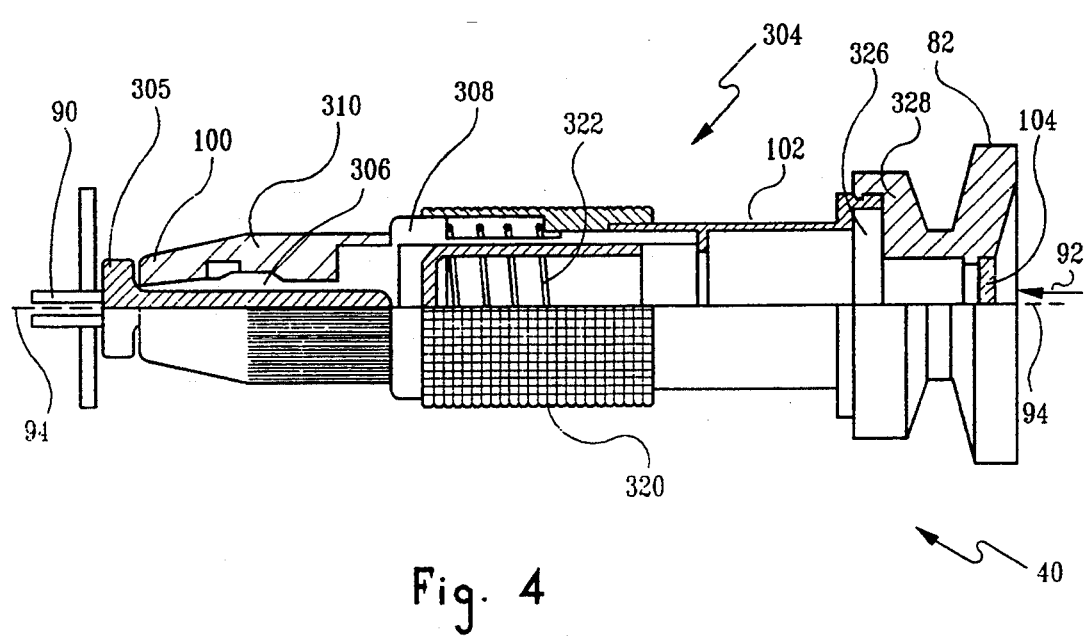
Fig. 4

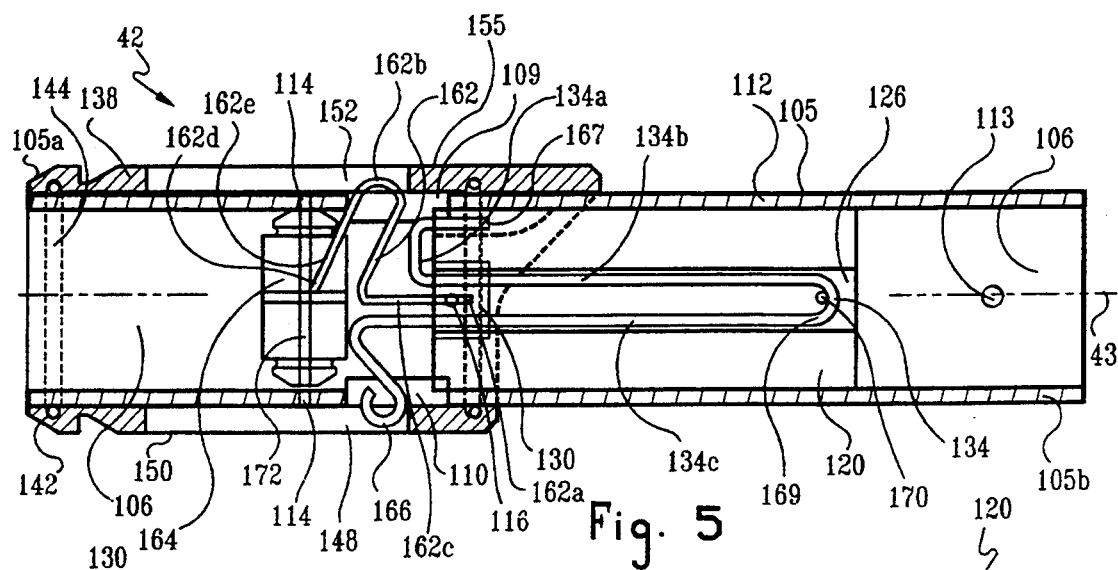

APPARATUS AND METHOD FOR ENDOSCOPIC DIAGNOSTICS AND THERAPY

BACKGROUND OF THE INVENTION

1. Field

This invention relates to optically assisted surgical procedures. More particularly, this invention provides novel apparatus and methods for conducting minimally invasive endoscopic diagnostic and therapeutic procedures.

2. State of the Art

Endoscopic methods and instruments for accessing body cavities, while well developed, do not adequately address several specific problems. Certain such instruments, as applied for diagnostic purposes, are regarded as being undesirably invasive. Others presuppose applications which are procedurally convoluted and prohibitively time-consuming. Some procedures require excessively complicated and costly structure and imaging components.

Typical endoscopic instruments and their customary applications include hysteroscopes for intra-uterine evaluation, amnioscopes for direct fetal diagnostics within the amniotic sac, falloposcopes for fertility enhancement, cystoscopes for bladder inspection, and ureteroscopes for renal access, general fiberscopes and the like. In some respects, trocar cannulae in conjunction with abdominal insufflation and other surgical equipment under endoscopic visualization may be considered as being related to the art of endoscopy.

Standard among existing endoscopic devices are eyepieces which are adaptable to varying focal depths. These eyepieces are characteristically fixed in position relative to the body of the scope. Fixed eyepieces limit the breadth and positing of the endoscope, imposing concomitant discomfort to the user and potential disruption at the insertion site. On average, for example, hysteroscopic diagnostic procedures have a duration of at least 5 minutes. Beyond the first few minutes of a procedure, the examiner ordinarily experiences discomfort, because the fixed position of the eyepiece restricts the examiner to a crouched position.

Conventional endoscopes may be either flexible or rigid in character. Currently available flexible endoscopes have outside diameters as small as 3.6 millimeters while conventional rigid endoscopes have outside diameters in the range of 6 millimeters to approximately 12 millimeters. The smaller, flexible endoscopes offer directional capability at their distal, leading end tips. They are by their nature, however, difficult to direct during insertion into a desired site. After surgical use, it is difficult to assure adequate and cost-effective sterility, particularly along the entire length of the channels characteristically incorporated within such flexible endoscopes for the delivery of distention media.

Endoscopes of relatively large outside diameter, whether rigid or flexible, present the disadvantage of invasive and obtrusive size. Preparatory procedures are required to address the potential for discomfort, infection due to inadequate sterilization following multiple procedures, and localized tissue trauma. Rigid scopes are inherently limited in their achievable distal orientations.

Common practice prescribes a protocol of local or general anesthetic preceding an hysteroscopic procedure. Several practical disadvantages, including cost and coordination requirements, arise from the involvement of anesthesia in hysteroscopy. The side-effects and risks associated with anesthesiological practice are also of concern. While some existing flexible hysteroscopes of smaller outside diameter avoid the disadvantages of anesthetization, the other disadvantages associated with flexible endoscopes may be especially pronounced in the context of hysteroscopy.

Conventional hysteroscopic practice involves steps to dilate the internal diameter of the cervix. It is desirable to minimize frictional resistance between the outside diameter of the hysteroscope and the inside periphery of the cervical orifice during insertion of the hysteroscope. Dilation of the cervical orifice has in most cases heretofore been accomplished by insertion of a strand of a substance, known as laminaria, derived from ground seaweed. The laminaria, following waiting periods not uncommonly in excess of 72 hours, gradually absorbs surrounding moisture and thereby expands to a diameter adequate for reception of a conventional hysteroscopic apparatus. It is necessary that dilation occur gradually to minimize discomfort. There are self-evident disadvantages to the laminaria dilation procedure. The procedure involves the cost of insertion and eventual removal under controlled conditions. An inordinate time commitment is required of the patient. This procedure also presents the possibilities of over expansion of the cervix and internal or external dislodging of the laminaria.

Another problem commonly encountered during hysteroscopic diagnostics is interference from source conduits for distention media. These conduits are typically stiff. When affixed in conventionally immovable relation to the body of hysteroscopic instruments, they tend to restrict the ease with which the instruments can be manipulated through the cervix and within the uterus.

A majority of hysteroscopic instruments comprise rigid cannula, through which illumination and image fibers are placed. The tips of the fibers protrude only minimally beyond the distal tip of the cannula. Because of the pear-like configuration and size of a distended uterus, most positions on the inner walls of the uterus can be acceptably visualized at the eyepiece despite employment of a rigid distal tip on the instrument. However, those portions of the inner uterine walls immediately adjacent the fallopian tubes can be only peripherally and poorly accessed. To achieve even this limited examination requires forcing the hysteroscopic instrument at an abrupt angle against the internal side of the cervical orifice opposite the internal wall of the uterus sought to be visualized. Patient discomfort and tissue damage are the probable consequences of such procedures.

Cost-effective and reliable sterilization of hysteroscopes has heretofore not been achieved. Contaminants tend to accumulate within the source conduit which conveys the distention medium. Microorganisms migrate and propagate within the elongate cannula. There is accordingly a degree of uncertainty in the efficacy of conventional sterilization procedures as applied to these instruments. Antibiotics utilized for disinfection in this context, aside from being extremely noxious and offensive to a user, are most often used as a soaking solution for roughly 20 minutes rather than the several hours necessary to more certainly assure adequate sterilization. Similarly, thorough cleansing manipulations applied to the optics themselves tend to cause fragmentation of the optics. Compromised optical clarity disrupts the quality of the light and visual images conveyed through the instrument.

It is currently normal practice for hysteroscopes to be non-disposable, primarily because of their sizable cost, and because their respective configurations have not readily lent themselves to fashioning them with disposable parts.

A need, therefore, exists in the art for an improved fiberscopic device structured to avoid the limitations and shortcoming of currently available such devices. Specifically, a need exists for an endoscopic device which avoids many of the practical disadvantages normally associated with general and local anesthetics. Further, a need exists in the art for an endoscopic device which is capable of maintaining some frictional resistance between the device and the insertion site without dilation of the insertion site. A need also exists in the art for a endoscopic device which incorporates mechanical and ergonomic enhancements to facilitate ease and precision of use for the user and comfort, safety, convenience and cost-effectiveness of use for the patient. There is a particular need for a structure which enables improved sterilization of reusable parts and facile disposability of single-use parts.

SUMMARY OF THE INVENTION

The present invention provides novel fiberscopic, typically endoscopic, devices wherein a substantially reusable but optionally partially disposable instrument is comprised of relatively few, efficiently manufacturable parts. It is easily assembled from few and inexpensive, readily available materials. It may be constructed so as to be cost-effectively and reliably sterilized.

Instruments may be embodied in accordance with this invention to be particularly well suited for use in connection with mammalian, in particular human, medicine including without limitation hysteroscopes for intra-uterine evaluation, amnioscopes for direct fetal diagnostics within the amniotic sac, falloposcopes for fertility enhancement, cystoscopes for bladder inspection, ureteroscopes for renal access and for scopes utilized for ear, nose and throat diagnostics, general fiberscopes and the like.

The endoscopic devices of this invention may be embodied to include a cannula insertion assembly of maximum outside diameter of as small as approximately 2 millimeters, more typically 3–6 millimeters. Specific embodiments may further incorporate one or more of a directionally adjustable eyepiece, ergonomically designed handle and mechanisms for manipulating the directional orientation of a distal optics tip. They may be structured to avoid many of the practical disadvantages normally associated with general and local anesthetics.

A fiberscopic instrument of this invention may comprise a handle, having a longitudinal handle axis, and a body, having a longitudinal body axis, a proximal end and a distal end. The body is ordinarily connected to the handle such that the handle axis is positioned transverse the body axis. The relative positioning of the handle and body axes is selected (and may be adjustable) as appropriate to assure efficient and practical manipulation of the instrument in an operatory environment. A fiber optic bundle, having a proximal end and a distal end corresponding to the proximal and distal ends, respectively, of the body, is housed within the body approximately parallel the body axis. Typically, the axis of the fiber bundle is approximately congruent with the longitudinal axis of the body.

An eyepiece will typically be structurally associated with the body and the proximal end of the bundle. Normal constructions place the longitudinal axis of the eyepiece approximately in a common plane with the axis of the body. Certain embodiments incorporate an eyepiece arrangement in which the ocular end of the eyepiece is fixed in position. The preferred embodiments incorporate a coupling structure, however, connecting the eyepiece to the body through a joint. This joint may be constructed and arranged to permit travel of the ocular end of the eyepiece with respect to the body. In this fashion, the relative orientations of the body axis and the eyepiece axis may be adjusted to suit the convenience of one using the eyepiece to observe an operating site. Various versions of the point permit pivotal movement along one or more coordinate axes, or in some instances, universal movement.

Adapting structure may be associated with the proximal end of the bundle, being constructed and arranged to interface the proximal end of the bundle to an eyepiece. An elongate eyepiece fixture may be structurally associated with the body and the adapting structure. Such an eyepiece fixture will have a longitudinal axis connecting an ocular end and an objective end, the objective end being coupled in light transmitting association with the bundle through the adapting structure. The adapting structure may comprise coupling structure, connecting the eyepiece to the body and constructed and arranged to permit travel of the ocular end of the eyepiece fixture with respect to the body, whereby to adjust the relative orientations of the body axis and the eyepiece axis. The coupling structure ideally includes an articulating or pivot joint between the body and the eyepiece.

It is often advantageous for the eyepiece to be removable from the remainder of the instrument, both to accommodate cleaning and to facilitate utilizing the eyepiece with other devices. Thus, the instruments of this invention may be provided with fixtures at the proximal end of the bundle adapted to couple to interchangeable eyepieces, video monitors or other equipment capable of accepting the fiber bundle as an input device. Such a fixture may be stationary, but it may also advantageously be incorporated structurally with an articulating joint of the type contemplated for accommodating travel of the eyepiece or other ocular device.

Typical fiberscopic instruments of this invention include a hollow sheath, carried internal the body. The sheath is usually formed as a conduit, typically of approximately circular cross section. The longitudinal sheath axis is oriented approximately parallel, often congruent with, the body axis. The distal end of the sheath extends from the body beyond the distal end of the body. Any number of cannulae may be included within the sheath to accommodate utilities or tools as appropriate. In any case, the fiber optic bundle is housed within the sheath approximately parallel the body axis. Ideally, the distal end of the bundle is movable axially with respect to the distal end of the sheath. Retractor structure is mechanically associated with the body, and is constructed and arranged for manual manipulation. Such manipulation selectively advances or retracts the distal end of the sheath with respect to the distal end of the bundle. Thus, it is feasible to advance the sheath through a barrier to the vicinity of an operation site with the bundle retracted, and to thereafter further advance the distal end of the bundle.

An optics encasement may be reciprocally mounted within the sheath. The encasement is then mechanically linked to the retractor structure and the fiber bundle is contained within the encasement. The distal end of the encasement normally terminates near the distal end of the bundle, the distal end of the bundle desirably extending only slightly beyond the terminus of the encasement. While the encasement may be substantially rigid, at least its distal end is preferably flexible and associated with mechanical linkage accessible from outside the instrument. The linkage structure may be operable to manipulate the orientation of the distal end of the encasement with respect to the longitudinal axis of the encasement. A preferred linkage structure connects the distal end of the bundle (or encasement) to the retractor. The retractor then constitutes remote means for at least moderately bending the distal tip of the objective end of the fiber bundle.

In a preferred configuration, the sheath is slidably mounted with respect to the body axis and the fiber bundle is fixed longitudinally with respect to the body. The distal end of the bundle is advanced with respect to the distal end of the sheath by sliding the sheath towards the proximal end of the body. The bundle is best contained within a flexible optics encasement, the distal end of which extends through the sheath. The sheath may comprise a unitary sheath assembly which includes a sheath seal constructed and arranged to effect a sliding, substantially fluid tight seal between the encasement and the sheath. The sheath assembly may be disposably removable from the body; that is, this assembly may be discarded after a single use, leaving the remainder of the instrument to be sterilized.

In a typical arrangement, an optics encasement, having a nominal longitudinal encasement axis, a proximal end and a distal end extends through a disposable sheath and contains a fiber optic bundle having both illuminating and image components. The bundle is oriented within the body approximately concentric with the sheath and with the distal end of the bundle extending slightly past the distal end of the encasement. The sheath is moveable between a distal position, in which the encasement is substantially within the sheath, and a proximal position, in which a distal portion of the encasement projects beyond the distal end of the sheath. The projecting distal portion of the encasement and the associated bundle are preferably sufficiently flexible to respond to mechanical manipulations, whereby to permit the objective end of the bundle to be oriented to a line of sight transverse the body axis and the sheath axis.

A retractor structure may be variously configured, and it may be mechanically associated with the body in various ways. For example, it may be constructed and arranged for manual manipulation between selected axial positions, thereby driving a protective sheath to corresponding proximal, distal and intermediate axial positions. It may further be constructed and arranged for manual manipulation to selected radial positions of rotation with respect to a reference axis, thereby driving a linkage structure to alter the line of sight of the fiber bundle. First and second such radial positions may correspond, for example, to a substantially axial and significantly canted-from-axial lines of sight. Intermediate radial positions will correspond to lines of sight which depart relatively less from axial. The canted lines of sight achievable with various embodiments may be transverse to the body axis at minor or major angles. In preferred constructions, the retractor and linkage structures are cooperatively constructed and arranged so that the linkage structure is operable in response to radial movement of the retractor only when the retractor is in or near its proximal position.

Certain preferred embodiments provide for the delivery of distention fluids through a sheath. Delivery may be through a cannula within the sheath or through an annular or other space defined by the sheath and the bundle within the sheath. This arrangement facilitates the introduction and retention of a distention medium within an expandable body cavity. It can thereby maintain a low level of frictional resistance between the sheath and the insertion orifice or aperture without the need for preparatory dilation of the insertion site. This capability significantly reduces the need for general anesthetic and permits procedures to progress with at most local anesthetic. The discomfort and tissue trauma currently experienced by a medical patient during insertion, manipulation and retraction of hysteroscopes, for example, are substantially alleviated by this invention.

Practical sheaths may have an outside diameter between about 3 and about 6, typically about 3½, millimeters. Practical fiber optic bundles may be less than 1 millimeter in diameter. The sheaths may be of sufficiently thin wall construction to leave an annular flow path of sufficient cross sectional area to accommodate practical flow rates of distention fluids of even significant viscosity. Flow rates of 100 milliliters per minute, for example, are routinely achievable.

The hysteroscopes of this invention significantly reduce frictional resistance between the hysteroscope and the internal wall of the undilated cervical channel while maintaining a sealing contact therebetween. A medical practitioner is thereby enabled to introduce the necessary amount of saline solution, $CO_2$ gas or other desired distention medium within the uterine cavity with only minor, if any, leakage of the distention fluid. Additionally, reduction of friction to a minimum prevents, relieves or reduces patient discomfort. A further benefit to the reduction of friction offered by this invention is an increased latitude for facile manipulation of the hysteroscope throughout the surgical procedure. Trauma to the cervical tissue associated with such manipulation when the inserted scope is situated interjacent difficult to reach diagnostic sites such as positions near the Fallopian tube uterine entrances is significantly reduced.

A sheath assembly, whether or not disposable, may be adapted to receive distention fluid at or near its proximal end. The sheath and the encasement define a fluid conveying passageway, which may be annular, for the transport of fluid to the distal end of the sheath. The sheath seal component of the assembly is positioned to block backflow of fluid towards the body of the instrument. A typical arrangement positions a resilient annular seal within the annular space between the interior surface of a sheath and the exterior surface of a bundle, or more typically a bundle encasement.

BRIEF DESCRIPTION OF THE DRAWINGS

In the drawings, which illustrate what is currently regarded as the best mode for carrying out the invention:

FIG. 1 is a perspective view, partially in section and partially in phantom lines, illustrating one fully-assembled embodiment of an endoscopic device of the invention, an alternative position of an eyepiece component being shown in phantom lines;

FIG. 2 is an enlarged fragmentary cross-sectional view of an articulating joint portion of the device of FIG. 1;

FIG. 3 illustrates structure alternative to that of FIG. 2, and includes FIG. 3A, a view in cross-section, FIG. 3B, a plan view taken along the reference line 3B—3B of FIG. 3A, and FIG. 3C a view in elevation taken along the reference line 3C—3C of FIG. 3B;

FIG. 4 is a side view in elevation, partially in section, of an eyepiece assembly of the invention;

FIG. 5 is an enlarged cut away view of a proximal end portion of a body assembly of the device of FIG. 1;

FIG. 6 is a side view in elevation, partially in phantom lines, of a "return to zero" (rtz) mount member of the device illustrated by FIG. 5;

FIG. 7 is a view in cross-section of the rtz mount of FIG. 6, taken along reference line 7—7 of FIG. 6;

FIG. 8 is a view in cross-section of a retractor member of the device illustrated by FIG. 5;

FIG. 9 is a bottom plan view of the retractor member of FIG. 8;

FIG. 10 is a top plan view of the retractor member of FIGS. 8 and 9;

DETAILED DESCRIPTION OF THE ILLUSTRATED EMBODIMENTS

Figure 11:
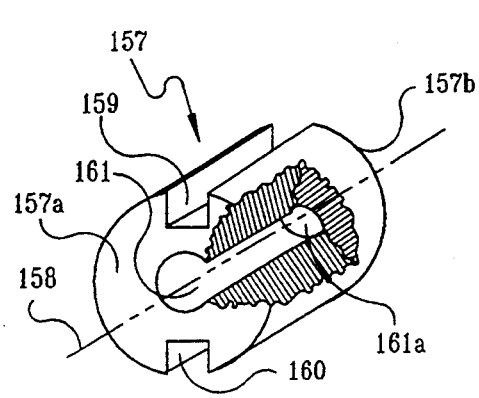
FIG. 11 is a cut away perspective view of a bobbin member of the device illustrated by FIG. 5.

The components of the present invention, as generally described and illustrated in the drawings, could be arranged in a wide variety of configurations. One embodiment of the invention constructed as an hysteroscope will be described with specific reference to the drawings, wherein like parts are designated by like numerals throughout.

Referring particularly to FIG. 1, a fiberscopic device 36 includes generally, a handle 37, an eyepiece assembly 40, a body assembly 42, (having a longitudinal axis 43), a sheath 45 having a distal end 45a, a proximal end 45b and an axis 45c) and an assembly of optical fibers. i.e., a bundle 48, (having a distal tip end 48 a, an illumination optics component 48b, FIG. 2 and an image optics component 48c).

As depicted in FIG. 1, the handle 37 is situated relative to the body 42 of the device 36 in a position that facilitates ergonomic clasping by a user during use. The handle is shown in its presently preferred orientation, extending downward at an approximately degree angle from the axis 43 of the body assembly 42 of the device 36. Of course, other configurations may be found to be more appropriate for fiberscopic devices intended for other specific applications.

The handle 37 includes exterior surface relief 50 to enhance the grip of a user. A preferred version of the relief 50 includes depressions 52 encircling the handle in series transverse the axis 54 of the handle 37 along the majority of the handle 37.

The transverse cross-section 56 (FIG. 3C) of the handle 37 is shown structured in a modified oval shape ergonomically to enhance comfort of use and relieve finger muscle tension during protracted procedural manipulation. Though not depicted in the FIGS., a handle 37 including, without limitation, exterior surface contours of modified general shape or customized to the contours of the palm or fingers or both of a user are specifically contemplated.

Referring to FIG. 1, a bore 60 extends from the heel 62 of the handle 37 to an interface void 65 between the handle 37, body assembly 42 and eyepiece assembly 40 (FIGS. 1, and 3A). Referring to FIG. 2, the bore 60 accommodates illuminating optics 48b which traverse the entire length of the handle 37, and continuing on, extend with image optics 48c through the body assembly 42 of the device 36 to the distal tip end 48a (FIG. 1) of the fiber bundle 48.

The handle 37 may include a channel 75 (FIG. 1) for securing a line 77 through which fluid can be communicated frown a source to the device 36. The channel 75 may be formed through the handle 37 in tunnel configuration similar to the bore 60. Alternatively, the channel 75 may be configured as a canal formed in the exterior surface of the handle 37 or structured in the form of clips along the exterior surface of the handle 37. Any of these or equivalent configurations of the channel 75 function to prevent the line 77 from interfering with an endoscopic procedure. They also safeguard against the line's becoming pinched or crimped, thereby assuring continued fluid flow.

The interface void 65 between the handle 37, eyepiece assembly 40 and body assembly 42, as illustrated by FIGS. 1 and 2, includes a cylindrical pivot joint 80 enabling the eyepiece assembly 40 to pivot in one vertical plane down and backward toward the heel 62 of the handle 37 or up and forward toward the distal tip end 48a, of the fiber bundle 48 as shown by phantom lines in FIG. 1. The proximal end 82 of the eyepiece assembly 40 remains a constant distance from the point of pivotal rotation.

An alternative interface 83 shown by FIG. 3A includes a ball joint 85 situated within a seating rack 87. The seating rack 87 is affixed to the handle 37 with pins 88a and 88b, bolts, adhesive or the like. A seal and gland 89 may be incorporated between the ball joint 85, the handle 37 and the seating rack 87. The ball joint 85 may be formed integrally, but is shown removable. As illustrated, an optic stub 90 is provided with a longitudinal tunnel 91 therethrough. The eyepiece assembly 40 of FIG. 1 is removably affixed to the device 36 by insertion of the optic stub 90 into a visual path 92, FIGS. 1 and 4, which opens within the eyepiece assembly 40 along its entire longitudinal axis 94.

Latitude and direction of available movement of the ball joint 85, FIG. 3A, may be determined by a joint frame 96 (FIG. 3B). A frame window 98 formed within the joint frame 96 defines the distance and direction of permissible travel of the eyepiece assembly 40. A slot-shaped joint frame 96 permits travel in a selected horizontal, vertical or diagonal plane. Other travel constraints may be provided by open circular, square, triangular or other geometrically shaped joint frames.

The eyepiece assembly 40, shown generally in FIG. 1 and specifically in FIG. 4, is comprised of a nose 100, a proximal eyepiece end 82, a visual media coupling 102 and the visual path 92 with desired lenses 104 at appropriate positions along the visual path 92. The visual media coupling 102 renders the proximal end 82 of the eyepiece assembly 40 removable. The visual media coupling 102 may also serve either a zoom or focusing function or both a zoom and focusing function. When the proximal end 82 of the eyepiece assembly 40 is removed, a selected visual medium, such as a video camera and cathode ray tube monitor with or without a remote video cassette recorder and/or video printer can be coupled to the eyepiece assembly 40 in conventional fashion for enhanced visual observation during an endoscopic procedure.

Though not specifically described, focusing and zoom means are contemplated as a part of the eyepiece assembly 40, as well as wide-angle means along the path of the optical fibers 48, FIG. 1. Also contemplated are lens systems at appropriate points along the path of the optical fiber bundle 48 whereby visual images conveyed along the bundle 48 are reoriented so as to appear to the observer as actually orientated at the site being visualized.

The body 105 of the body assembly 42 of the device 36, (as illustrated in FIGS. 1, 2 and 5) has a distal end 105a, a proximal end 105b, and defines an elongate cylindrical space 106. As a part of the assembled device 36, the body 105 proximal end 105b is snugly situated through and resides within an anterior hole 107 in the handle 37, shown most clearly in FIGS. 2 and 3A. Referring to FIGS. 1 and 5, a top window 109 and a bottom window 110 are formed in the body 105 opposite each other through the body wall 112. If pin 88a of FIG. 3A is utilized to anchor the seating rack 87 about the interface void 65, then pin holes 113 (FIG. 5) through which pin 88a is to be inserted may be formed in the wall 112 of the body 105. The body 105 also incorporates spindle postholes 114 and a mount pinhole 116 for similar anchoring functions.

Referring generally to FIG. 5 and particularly to FIGS. 6 and 7, a cylindrical return to zero (rtz) mount 120 (having a distal end 120a and a proximal end 120b) is shown in one preferred embodiment of the present invention wherein the rtz mount 120 is situated within and concentric with the body 105 of the device 36. The rtz mount 120 along its entire exterior surface is in contact with a portion of the interior surface of the body 105 and may be anchored thereto in press-fit relation or alternatively with a body-mount pin 122 imposed within the mount pinhole 116 of FIG. 5 and the rtz body-mount pinhole 124. FIGS. 6 and 7.

Referring to FIGS. 5, 6, and 7, the rtz mount 120 defines a mount space 126 along the longitudinal axis 127 of the rtz mount 120. The mount space 126 may be of a round transverse cross-sectional configuration. The rtz mount 120 also defines a bobbin space 130 (FIGS. 6 and 7) at the distal end 120a of the rtz mount 120. The bobbin space 130 may likewise be of a round transverse cross-sectional configuration, but preferably of a diameter larger than that of the mount space 126. A groove 132 is formed radially at or near the exterior surface of the rtz mount 120 and opens at the distal end 120a of the rtz mount 120 to anchor the rtz spring 134, FIG. 5. The rtz spring has a leading end portion 134a, an tipper spring bar 134b and a lower spring bar 134c. The groove 132 (FIGS. 6 and 7) runs parallel the longitudinal axis 127 of the rtz mount 120. Routing channels 136 are formed in the exterior surface and on opposing sides of the rtz mount 120 parallel and along the entire longitudinal axis 127.

Shown generally in FIG. 5 and specifically in FIGS. 8, 9, 10, a typical retractor 138 (having a distal end 138a, a proximal end 138b and a longitudinal axis 138c) of the present invention defines a hollow space 140 (FIG. 8). The retractor 138 is cylindrical in shape, open at its distal end 138a and proximal end 138b and surrounds the external surface of the distal end 105a of the body 105 of the device 36 (FIG. 5). The internal surface of the retractor 138 is near to and surrounds the external surface of the body 105 of the device 36. It slidingly engages the external surface of the body 105 of the device 36, both longitudinally and radially, through the sealing rings 142 (FIG. 8) which are mounted into each of two twin recess annuli 144 (FIGS. 8–10). The retractor 138 is separated from the body 105 only by the two sealing rings 142, one at each end of the retractor 138. Each sealing ting 142 fits within a respective such recess annulus 144. At the distal end 138a of the retractor 138, a lip 146 is formed integrally with and around the external surface of the retractor 138.

An elongate narrow slot 148 (FIGS. 8 and 9) is formed entirely through the bottom wall 150 of the retractor 138. An elongate pear-shaped slot 152 (FIGS. 8 and 10, having a narrow distal end 152a and a wide proximal end 152b) is formed entirely through the top wall 155 of the retractor 138. Both the slot 148 and the slot 152 (viewed lengthwise) are disposed parallel the longitudinal axis 138c of the retractor 138 midway between the distal 138a and proximal 138b ends of the retractor 138.

A bobbin 157 (having a distal end 157a, a proximal end 157b and a longitudinal axis 158, FIGS. 5 generally and 11 specifically) is situated within the assembled device 36, its exterior surface being in contact with the interior surface of the bobbin space 130 of the rtz mount 120, FIGS. 6 and 7. The external surface of the bobbin 157 (FIG. 11) incorporates a top duct 159 and a bottom duct 160 parallel its longitudinal axis 158. The ducts 159, 160 extend from the distal end 157a to the proximal end 157b. The bobbin 157 also incorporates a bobbin core 161 beginning at the distal end 157a and extending to a seat 161a where the bobbin core 161 terminates short of the bobbin proximal end 157b.

FIG. 5 illustrates an rtz spring 134 which provides zero-biased torsion force to a retractor 138. The retractor 138 is mounted in association with an interacting rotator 162. The rotator 162 has a rotator end 162a, a rotator elbow 162b, a posterior post 162c, a nose 162d, and an anterior post 162e. Rotator 162 also interacts with associated spindle stub 164 (FIGS. 5 in general and 12 specifically). The spindle stub 164 includes a first end 164a, a second end 164b, a through hole 164c, a through path 164d, a first track 164e, a second track 164f, and a cone void 164g. The spindle stub 164 also has a longitudinal through hole 164c axis 165a, a transverse through path 164d axis 165b and a longitudinal cone void 164g axis 165c. The rtz spring 134 (FIG. 5) comprises a spring elbow 166, a stationery post 167 and an anchor joint 169. The stationery post 167 is situated within the groove 132 (FIGS. 6 and 7) of the rtz mount 120. As illustrated in FIG. 5, the leading portion 134a of the rtz spring 134, when in assembled position, is situated immediately adjacent the distal end 120a of the rtz mount 120 between the groove 132 and the bobbin space 130.

With the leading spring portion 134a in assembled position, the anchor joint is situated within the mount space 126. Accordingly, the entire rtz spring 134 may be held in position in combination with the seated stationery post 167 by a pin 170 (FIGS. 5, 6 and 7). As shown most clearly in FIG. 5, when so assembled the spring elbow 166 extends radially outward from the longitudinal axis 43 of the body 105 through the bottom window 110 and into the narrow slot 148 in the bottom wall 150 of the retractor 138 (FIGS. 8–10).

In such an assembled position, the upper spring bar 134b (FIG. 5) and lower spring bar 134c extend respectively through the top duct 159 and bottom duct 160 of the bobbin 157, FIG. 11.

As best illustrated by FIG. 5, the bobbin core 161 (FIG. 11) of the bobbin 157 is of sufficient size and transverse cross-sectional dimension to receive the posterior post 162c of the rotator 162 and to allow the posterior post 162c to rotate along the longitudinal axis 43 of body assembly 42. In assembled position, the rotator end 162a buts the seat 161a of the bobbin 157 (FIG. 11). As assembled, the rotator elbow 162b extends radially outward from the longitudinal axis 43 of the body 105 through the top window 109 of the body 105 and into the pear-shaped slot 152 in the top wall 155 of the retractor 138.

Figure 12:
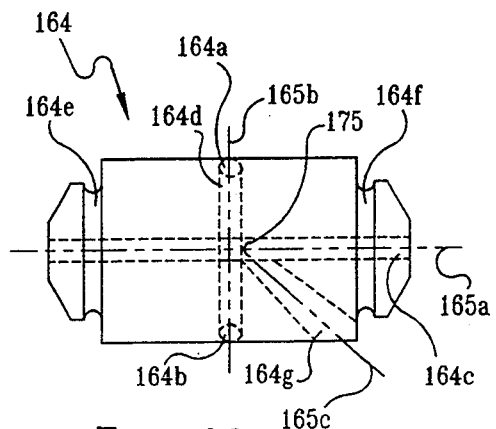
FIG. 12 is a side elevation view, partially in phantom lines, of a spindle member of the device illustrated by FIG. 5.

Depicted most simply in FIG. 12, the spindle stub 164 is shaped cylindrically and comprises a first stub end 164a, a second stub end 164b, a through hole 164c, a through path 164d, a first track 164e, a second track 164f and a cone void 164g. The through hole 164c is a space extending along the longitudinal axis 165a from the first stub end 164a to the second stub end 164b. The through hole 164c rotatingly accommodates a post 172 (FIG. 5) affixed at each end to spindle postholes 114 in the body 105. The through path 164d has a longitudinal axis 165b that is transverse and may be perpendicular to the longitudinal axis 165c of the spindle stub 164. The through path 164d, though not intersecting the through hole 164c directly, may at one transverse cross-section of its longitudinal axis 165b be positioned tangential to one transverse cross-section of the longitudinal axis 165a of the through hole 164c.

The spindle stub 164, illustrated in FIGS. 5 generally and 12 specifically, is positioned in the space 106 within the body 105, and as so positioned has a longitudinal axis 165a that is situated transverse the longitudinal axis 43 of the body 105. The first stub end 164a and second stub end 164b of the spindle stub 164 radially flare toward each other around their respective entire peripheries along curves that inversely follow the contours of the internal surface of the body 105 against which each stub end, 164a, 164b, is situated. This inverse mating of the ends, 164a, 164b, of the spindle stub 164 relative to the internal curved surfaces of the body 105 enables facile axial rotation of the spindle stub 164 when the spindle is in position. When the spindle stub 164 is in position, the through path 164d is approximately parallel (but not necessarily concentric with) the longitudinal axis 43 of the body 105.

The cone void 164g must be formed in the spindle stub 164 in sufficient size to accommodate the nose 162d of the rotator 162 at the point 175 of the cone void 164g and to allow the anterior post 162e of the rotator 162 to move freely vertically within the cone void 164g of the spindle stub 164 as the spindle stub 164 is rotated from side to side along its longitudinal axis 165c. Yet the cone void 164g is desirably sufficiently narrow laterally to hold the anterior post 162e snugly, yet movably, within the cone void 164g. In this fashion, the rotator 162 is coupled synchronously with the spindle stub 164.

When assembled (FIG. 5), the retractor 138, rotator 162, rtz spring 134, and spindle stub 164 move synchronously with one another. The retractor 138 may be manually externally clasped by a user and pushed by the user to slide the retractor 138 to a distal position in which the rotator elbow 162b is located within the wide proximal end 152b of the pear-shaped slot 152 (FIG. 10). In this distal retractor position, the pear-shaped slot 152 is precluded from engaging the rotator elbow 162b when the retractor 138 is rotated along its longitudinal axis 138c around the body 105 of the device 36 in either direction.

The retractor 138 alternatively may be manually externally clasped by a user and pulled by the user to slide the retractor 138 to a proximal position in which the rotator elbow 162b is located within the narrow distal end 152a of the pear-shaped slot 152. In this proximal retractor position the pear-shaped slot 152 engages the rotator elbow 162b when the retractor 138 is rotated along its longitudinal axis 138c around the body 105 of the device 36 in both directions, thereby moving the rotator 162 in the direction of rotation of the retractor 138.

As best seen from FIGS. 5 and 10, in the proximal retractor position, the narrow distal end 152a of the pear-shaped slot 152 engages the rotator elbow 162b. The rotator 162 may thereby be rotated, causing the anterior post 162e of the rotator 162 to engage the spindle stub 164 via the cone void 164g. The spindle stub 164 is thus caused to rotate along its longitudinal axis around the spindle post 172 in the same direction of rotation of the rotator 162. By this means, in the proximal retractor position, the retractor 138 synchronously moves the rotator 162 and the rotator in turn simultaneously moves the spindle stub 164 in a desired direction.

Figure 13:
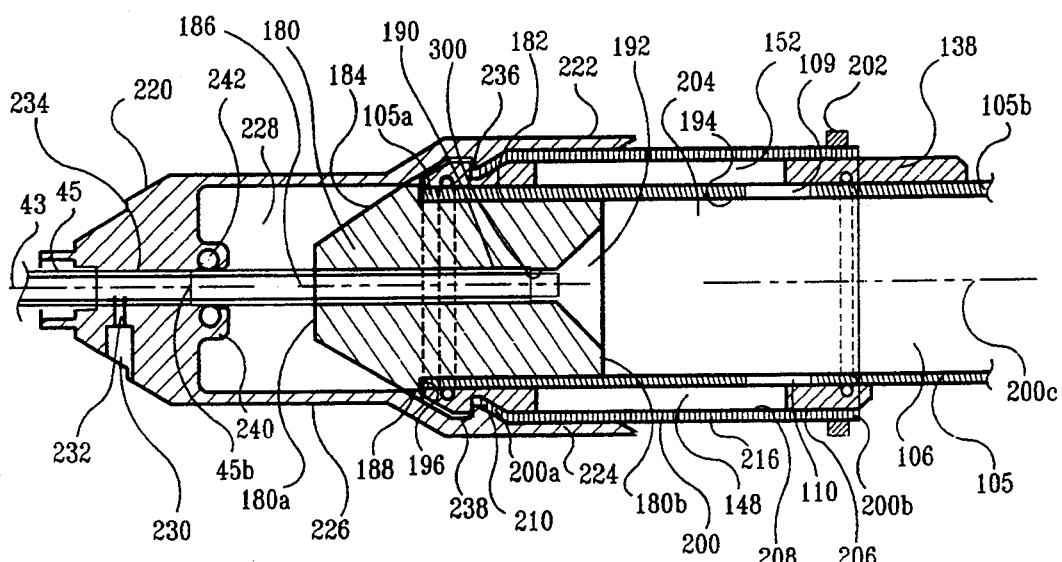
FIG. 13 is an enlarged cross-sectional view of a middle section of the body assembly of the device of FIG. 1.

A mounting hub 180 (having a distal end 180a and a proximal end 180b), illustrated most clearly by FIG. 13, is formed with a cylindrical exterior surface 182 at its proximal hub end 180b. The face 184 of the mounting hub 180 angles radially inward toward the longitudinal axis 186 of the mounting hub 180 toward the distal hub end 180a of the mounting hub 180 from a rim 188 located approximately mid-way along the length of the mounting hub 180. An encasement bed 190, having an approximately circular transverse cross-sectional shape, is formed along the longitudinal axis 186 of the mounting hub 180. The encasement bed 190 may open to a cone space 192 at the proximal hub end 180b. The cylindrical exterior surface 182 of the proximal hub end 180b is sized to seat within the body 105 and against the internal cylindrical surface 194 of the body 105. The rear face 196 of the rim 188 of the mounting hub 180 abuts the distal end 105a of the body 105 when the mounting hub 180 is so seated within the body 105.

Referring to FIG. 13, a sleeve 200 (having a distal end 200a, a proximal end 200b and a longitudinal axis 200c) is associated with a sleeve ring 202. The sleeve 200 is structured to define a sleeve space 204 within which the retractor 138 fits. The exterior surface 206 of the retractor 138 pressing snugly against the interior surface 208 of the sleeve 200. In assembly, the distal end 200a of the sleeve 200 is crimped along its entire periphery into the rut 210 of the retractor 138 (FIGS. 8–10) behind the lip 146. The sleeve 200 extends snugly along virtually the entire exterior surface 206 of the retractor 138, and shields the narrow slot 148 and the pear-shaped slot 152 of the retractor 138 from contaminants and extraneous debris.

The external surface 216 of the sleeve 200 may be provided with relief (not shown). The sleeve 200, in combination with the sleeve ring 202, may then accomplish the additional function of providing an improved grip when a user clasps and advances, retracts or radially rotates the retractor 138.

As shown by FIG. 13, a sheath seal 220 may comprise a first wing 222 and a second wing 224, a cylindrical sheath seal body 226 which defines a sheath space 228, a fluid port 230, a port neck 232, a sheath receptacle 234, a sheath hook 236, a rut void 238, a ring clasp 240 and an O-ring 242. The O-ring 242 fits snugly within the ring clasp 240. In assembled position, the sheath hook 236 radially slidingly engages the rut 210 of the retractor 138 as the lip 146 of the retractor 138 radially slidingly engages the rut void 238 of the sheath seal 220.

A distention fluid line 77 (FIG. 1) may be affixed within the fluid port 230 (FIG. 13) to abut the port neck 232. The fluid port 230 may open in the direction of the bottom of the device 36. The first wing 222 and second wing 224 extend proximally over the retractor 138 from the top and bottom of the device 36 respectively. In other embodiments, they may extend proximally over the retractor 138 from the sides of the device 36 or frown other radially opposing positions.

The wings 222, 224 may be structured of disposable material in a single use sheath assembly which may comprise a sheath 45 (having a distal end 45a a proximal end 45b and a longitudinal axis 45c) and sheath seal 220. In such an assembly, a user can achieve a nonreversible breaking off or bending away of the wings 222,224 from the retractor 138 when the sheath 45 and sheath seal 220 are sought to be removed from the device 36 and discarded by a user. This nonreversible break away capability prevents multiple use of this sheath assembly under circumstances in which single use is contemplated.

A sheath 45 (FIGS. 1 and 14) may be formed as an elongate rigid cannula. In its assembled position, the sheath 45 at its proximal end 45b is situated within the sheath receptacle 234. The exterior surface of the proximal end 45b of the sheath 45 is affixed in press-fit relation to the interior surface of the sheath receptacle 234 and may be bonded in place. The sheath 45 at its distal end 45a may radially curve slightly inward toward the longitudinal axis 43 of the sheath 45 to enhance insertability of the sheath 45 into a targeted site aperture or orifice, thereby to minimize pain of insertion.

The sheath seal 220 and sheath 45 may be formed of appropriate biocompatible plastics or other inexpensive, disposable material. The sheath seal 220 may likewise be available with sheaths 45 of varying outside diameters to ensure, without anesthesia, a degree of minimal yet adequate contact and friction along the interface between the exterior circumference of the sheath 45 and the interior circumference of the cervix of a patient for retention of distention medium.

The sheath 45 (shown in FIG. I generally and FIG. 14 specifically) defines a sheath space 257 along its entire length, the space opening at both the distal 45a and proximal 45b ends. The sheath space 257 accommodates the assembly of optical fibers. e.g., a bundle 48 as shown by FIGS. 1 and 2. The optical fiber bundle 48 comprise the illumination optics 48b and the image optics 48c. These fiber optic components 48b, 48c have distal ends 260 and 262, respectively (FIG. 16), and are bundled lengthwise with respect to each other and bonded in place within an optics encasement 264, including a rigid segment 265 (FIG. 14, having a distal end 265a, a proximal end 265b and a longitudinal axis 265c). The encasement 264 may be formed of a material that is rigid or flexible. As illustrated, the rigid segment 265 terminates at a termination point 267. Beyond that point, the encasement 264 is comprised of a flexible distal segment 268.

The bundle 48, which extends distally beyond the termination point 267, is immediately and essentially completely surrounded by a wire coil 270 extending to but not distally beyond the distal tip 48a. The portion of the bundle 48 covered by the wire coil 270 and exposed at the distal tip 48a is completely and snugly surrounded by an envelope 272. This envelope may be clear, particularly where it contacts the distal tip 48a of the bundle 48. The envelope 272 encompasses and is sealed in fluid-tight relation to the exterior surface 274 of the optics encasement 264 at the termination point 267.

A first guide wire 280 is affixed at its proximal end to the spindle stub 164 (FIG. 12) at one end 164a of a bore 164d. A second guide wire 284 is similarly affixed at a second end 164b of the bore 164d to the spindle stub 164. As shown, the guide wires extend within and through the optics encasement 264, FIG. 14. The first guide wire 280 is affixed at its opposite end to a first anchor point 288 inside the wire coil 270. The second guide wire 284 is affixed at its opposite end to a second anchor point 289 inside the wire coil 270. The first and second anchor points 288,289 are shown located approximately opposite each other.

Figure 14:
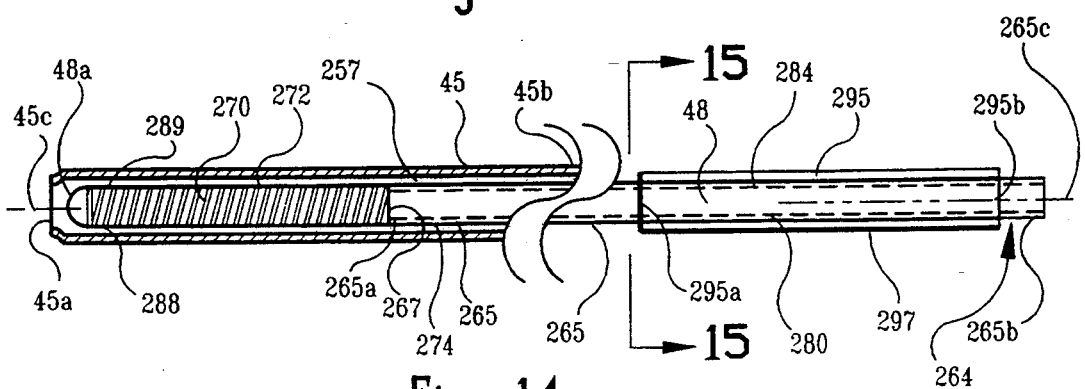
FIG. 14 is an enlarged cut away view of a distal end of a body assembly of the device of FIG. 1.

As illustrated by FIGS. 1, 5, and 14, when the retractor 138 is turned either clockwise or counter clockwise, it actuates the rotator 162, which in turn actuates the spindle stub 164, which in turn creates slack on one of the guide wires 280, 284, simultaneously creating tension on the other of the guide wires. Accordingly, when the retractor 138 is rotated to turn the spindle stub 164 in a direction which creates tension on the first guide wire 280, the second guide wire 284 becomes slack.

When tension is created on the first guide wire 280 to an increasing degree by further radial rotation of the retractor 138, the first anchor point 164a is further drawn proximally to a comparable degree, causing the distal tip 48a of the optical fiber bundle 48 to bend laterally in one direction commensurate with and in response to the radial rotation of the retractor 138. When the retractor 138 is radially rotated in the opposite direction, tension is created on the second guide wire 284, the second anchor point 164b is drawn proximally, likewise causing the distal tip 48a of the optical fiber bundle 48 to bend laterally, but in the other direction.

Figure 15:
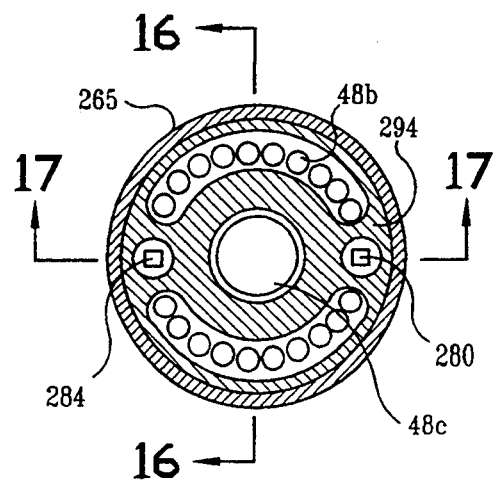
FIG. 15 is a view in cross-section of a sheath assembly, taken along reference line 15—15 of FIG. 14.
Figure 16:
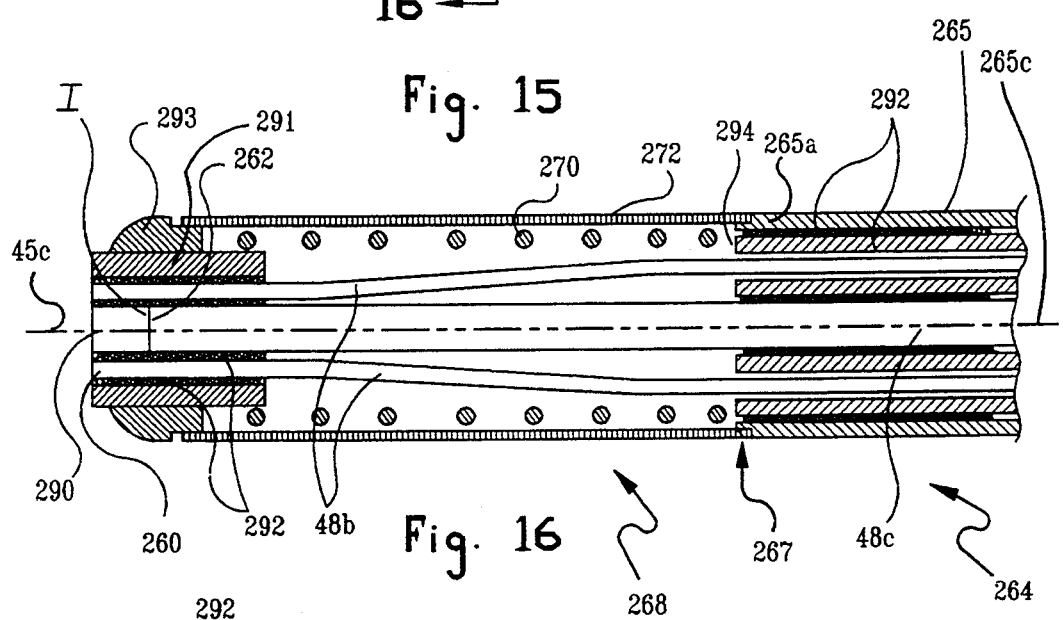
FIG. 16 is a view in cross-section, taken along reference line 16—16 of FIG. 15.
Figure 17:
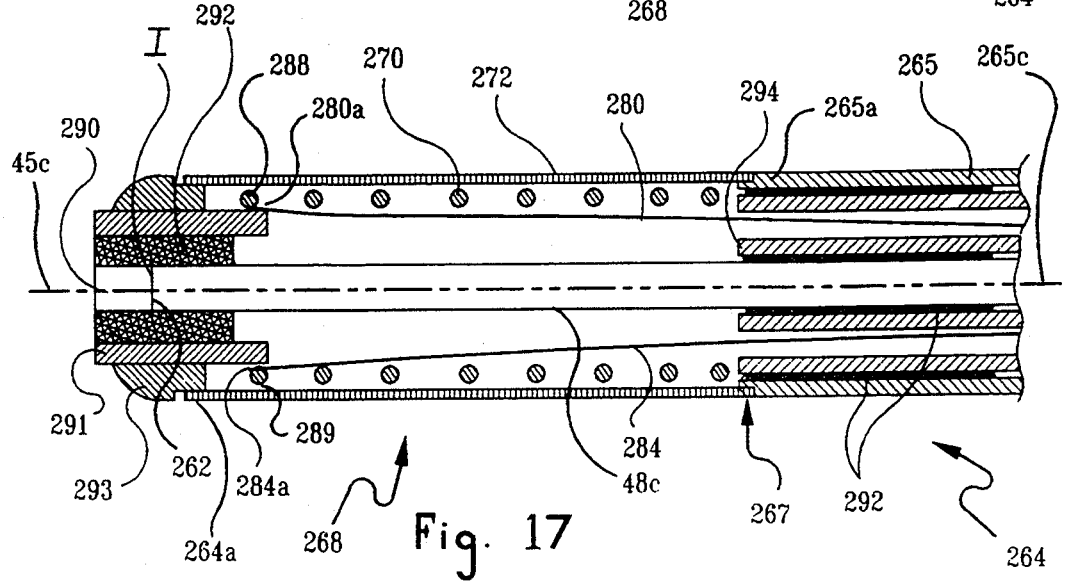
FIG. 17 is a view in cross-section, taken along reference line 17—17 of FIG. 15.

Referring specifically to FIGS. 15-17, the image fiber bundle 48c has an objective lens 290 at its distal end 262a which forms an image of objects under observation at the interface plane I. This image is transmitted via fiber bundle 48c, the field of vision and depth of view being determined by the characteristics of the lens 290. The distal end 262a of the image fibers 48c, the lens 290, and the distal end 260a of a plurality of illumination fibers 48b are captured by a lens housing 291, the interstitial spaces between these components being filled with a suitable potting compound 292. Cured epoxy resins selected for excellent biocompatibility and refractory (environmental resistance) properties are presently preferred. A ferrule 293 is bonded as shown around the lens housing 291, and provides a rounded tip contour which reduces the risk of tissue trauma. The distal ends of the bonded components, 260, 262, 291 and the bonding matrix 292 are polished co-planer with the objective surface of the lens 290.

The image fiber bundle 48c resides within a central lumen of a guide tube 294, FIG. 17. Other lumens of the guide tube 294 accommodate the illumination fibers 48b and the first and second guide wires, 280, 284. The image fiber 48c is bonded to the guide tube 294, as shown, while the illumination fibers 48b are not. The bonded optic fiber 48c is stiff in the axial direction, and it thus serves to space the lens housing 291 away from a jacket tube encasement 265. The guide wires 280, 284 are free to move axially within the guide robe 294 in response to manipulations of the spindle 164, FIG. 17. The distal ends 280a, 284a, respectively of the guide wires 280, 284 are bent and bonded as shown to the terminal coil of the wire coil spring 270. The interface of these components is adapted to ensure that the wires 280, 284 act upon the spring 270 at diametrically opposed locations. The spring 270 serves to contain and protect the wires 280, 284 and fiber ends 260, 262 when the envelope 272 encasing the spring 270 is deflected in use to change the direction of the line of sight of the lens 290.

A sleeve tube, or envelope, 272 is desirably placed between the ferrule 293 and the optics encasement tube 265 to improve the aesthetic appearance of the device 36, to present a smooth surface to tissue and to prevent the entry of debris and fluids into the deflecting tip structure.

At its proximal end 265b, the optics encasement segment 265 is surrounded by and bonded to a concentric tube 295 (having a distal end 295a, and a proximal end 295b. The concentric tube 295 comprises an exterior surface 297 of substantially uniform cross-sectional configuration and diameter along its entire length which is smaller than the internal transverse cross-sectional diameter of the sheath 45 (FIG. 14). When in assembled position, the proximal tube end 295b is situated within the encasement bed 190, FIG. 13. The exterior surface 297 of the concentric tube 295 at its proximal tube end 295b is affixed, around its entire periphery, against the interior surface 300 of the encasement bed 190.

The exterior surface 297 of the concentric tube 295 axially and radially slidingly engages the O-ring 242 when the retractor 138 is in the distal and proximal retractor positions relative to the body 105. As the retractor 138 is drawn proximally by a user, the O-ring 242 and the exterior surface 297 of the concentric tube 295 slidingly engage one another in a sealing relationship across the portion of the exterior surface 296 between the distal 295a and proximal 295b ends.

When the retractor 138 is in the distal retractor position, the sheath 45 encases the fiber optics 48 beyond the distal tip 48a (most clearly illustrated in FIGS. 13 and 14). Accordingly, in the distal retractor position, distention medium from the fluid line 77 may be introduced at the fluid port 230 through the port neck 232. The distention medium thereby gains access into an annular sheath space 257 between the optical fiber bundle assembly 48 and the sheath 45. It may flow freely through the annular sheath space 257 for introduction into an endoscopic site at the distal tip 45a of the sheath 45. The engagement between the O-ring 242 and the concentric tube 295 prevents distention medium from migrating proximally when the device 36 is in either the distal or proximal retractor position.

A typical eyepiece assembly 40, FIG. 4, and the manner in which it may be plug connected to an optical stud 90 (shown generally in FIG. 1 and in more detail in FIGS. 2–4) of an articulating joint assembly, designated generally 83. Referring to FIG. 4, an eyepiece coupler (102) assembly 304 comprises a plug coupler 305 (which may be an optical stud 90) insertable within the interior channel 306 of a housing body 308 within a collet 310. A focusing arrangement is provided by the focusing collar 320 acting against a compression spring 322 within the housing body 308, as shown, to change the separation distance between the end of the image bundle 48 and the modified objective lens 326. The eyecup 328 may be removed to permit use of auxiliary image processing devices with the camera adapter 102.

As best illustrated by FIGS. 2 and 3A, an articulating joint 83 comprises the junction of a handle 37 and an encasement (or body) tube 105 joined by a pin 88a (FIG. 3A) in a pin hole 113 (FIG. 2). An illumination fiber bundle component 48b exits the rtz mount 120, passes through the lumen 60 of the handle 37 to an appropriate light source (not shown). An image bundle component 48c exits from the rtz mount 120 and is routed through the lumen 340 of the optical stud 90 into a narrow lumen extension 342, wherein it is bonded with a suitable adhesive compound. The terminus 345 of the image bundle component 48c is polished flush with the end of the stud 90. The stud 90 is mounted, as shown in FIG. 2, in a through hole 348 in the pivot member 80 (FIG. 2) or 85 (FIG. 3A) which is pivotably mounted within a transverse channel 352 in the handle 37. The outer surface of the pivot member 80 is provided with a groove 355 concentrically disposed with respect to the through hole 348. The groove 355 accommodates an O-ring seal 358, which is positioned to exclude fluids leaking from the interiors of the handle 37 and tube 105. The seal and gland 89 (FIG. 3A) illustrated for a ball 85 pivot joint serves the same function as the groove 355 and O-ring seal 388 (FIG. 2) illustrated for a cylindrical 80 pivot joint.

A saddle 360 (FIG. 2), which serves to enhance the cosmetic appearance of the instrument, includes a clearance hole 362 which accommodates the stud 90. Appropriately located pivot holes 364 and pins 366 permit the saddle 360 to rotate with the pivot member 80. The pin 366 may extend beyond the walls of the handle 37 sufficiently to register with cooperating structure adapted to lock the stud into predetermined selected positions.

The present invention provides an improved fiberscopic structure and attendant methods for various forms of endoscopy. The present invention may be embodied in a variety of specific forms without departing from its essential characteristics. The described embodiments are to be considered in all respects only as illustrative, and not restrictive. The scope of the invention is, therefore, indicated by the appended claims, rather than by the foregoing description. For example, it is within contemplation that the annular space defined between the sheath and the cannula may be partitioned by means of rigid or compressible baffles into a plurality of fluid flow channels. Distension or other fluids may be introduced and/or withdrawn through any of these channels as well as any flow channels provided within the cannula itself. A surgical or exploratory site may be flushed by introducing fluid through one such channel and withdrawing that fluid through another such channel. These and similar modifications to the foregoing description which come within the meaning and range of equivalency are to be embraced within the scope of the appended claims.

What is claimed and desired to be secured by United States Letters Patent is:

1. A fiberscopic instrument, comprising:
   a handle, having a longitudinal handle axis;
   a body, having a longitudinal body axis, a proximal end and a distal end, said body being connected to said handle such that said handle axis is transverse said body axis;
   a fiber optic bundle, having a proximal end and a distal end, said bundle being housed within said body approximately parallel said body axis with the distal end of said bundle extending past the distal end of said body;
   an eyepiece, having a longitudinal eyepiece axis, said eyepiece being structurally associated with said body and said proximal end of said bundle; and
   articulating coupling structure, connecting said eyepiece to said body, constructed and arranged to permit travel of said eyepiece with respect to said body, whereby to adjust the relative orientations of said body axis and said eyepiece axis.

2. A fiberscopic instrument, comprising:
   a handle, having a longitudinal handle axis;
   a body, having a longitudinal body axis, a proximal end and a distal end, said body being connected to said handle such that said handle axis is in approximately the same plane as said body axis;
   a hollow sheath, having a longitudinal sheath axis, a proximal end and a distal end, said sheath being carried by said body approximately parallel said body axis, the distal end of said sheath extending beyond said distal end of said body;
   a fiber optic bundle, having a proximal end and a distal end, said bundle being housed within said sheath approximately parallel said body axis with the distal end of said bundle being movable axially with respect to the distal end of said sheath;
   adapting structure associated with said proximal end of said bundle, constructed and arranged to interface said proximal end of said bundle to an eyepiece; and
   retractor structure mechanically associated with said body, constructed and arranged for manual manipulation selectively to advance or retract said distal end of said sheath with respect to said distal end of said bundle.

3. A fiberscopic instrument, comprising:
   a handle having a longitudinal handle axis;
   a body having a longitudinal body axis, a proximal end and a distal end, said body being connected to said handle such that said handle axis is in approximately the same plane as said body axis;
   a hollow sheath, having a longitudinal sheath axis, a proximal end and a distal end, said sheath being carded by said body approximately parallel said body axis, the distal end of said sheath extending beyond said distal end of said body;
   a fiber optic bundle, having a proximal end and a distal end, said bundle being housed within said sheath approximately parallel said body axis with the distal end of said bundle being movable axially with respect to the distal end of said sheath;
   adapting structure associated with said proximal end of said bundle, constructed and arranged to interface said proximal end of said bundle to an eyepiece; and
   retractor structure mechanically associated with said body, constructed and arranged for manual manipulation selectively to advance or retract said distal end of said sheath with respect to said distal end of said bundle,
   further including an optics encasement, having a longitudinal encasement axis, proximal end and a distal end, extending through said sheath and containing said bundle, said encasement being mechanically linked to said retractor structure.

4. An instrument according to claim 3 wherein said distal end of said encasement terminates near said distal end of said bundle.

5. An instrument according to claim 3 wherein said encasement is flexible, said instrument including mechanical linkage structure between said distal end of said encasement and said retractor structure, said linkage structure being operable to manipulate the orientation of said distal end of said encasement with respect to said encasement axis.

6. An instrument according to claim 2 including an eyepiece, having a longitudinal eyepiece axis, said eyepiece being mountable to said adaptor structure to be structurally associated with said body and said proximal end of said bundle with said eyepiece axis in approximately the same plane as said body axis.

7. A fiberscopic instrument, comprising:
   a handle, having a longitudinal handle axis;
   a body, having a longitudinal body axis, a proximal end and a distal end, said body being connected to said handle such that said handle axis is in approximately the same plane as said body axis;
   a hollow sheath, having a longitudinal sheath axis, a proximal end and a distal end, said sheath being carried by said body approximately parallel said body axis, the distal end of said sheath extending beyond said distal end of said body;
   a fiber optic bundle, having a proximal end and a distal end, said bundle being housed within said sheath approximately parallel said body axis with the distal end of said bundle being movable axially with respect to the distal end of said sheath;
   adapting structure associated with said proximal end of said bundle, constructed and arranged to interface said proximal end of said bundle to an eyepiece; and
   retractor structure mechanically associated with said body, constructed and arranged for manual manipulation whereby selectively to advance or retract said distal end of said sheath with respect to said distal end of said bundle,
   wherein said sheath is slidably mounted with respect to said body axis and said fiber bundle is fixed longitudinally with respect to said body, whereby said distal end of said bundle is advanced with respect to said distal end of said sheath by sliding said sheath towards the proximal end of said body.

8. An instrument according to claim 7 including an optics encasement, having a longitudinal encasement axis, proximal end and a distal end, extending through said sheath and containing said bundle, said encasement being mechanically linked to said retractor structure.

9. An instrument according to claim 8 wherein said encasement is flexible at its distal end, said instrument including mechanical linkage structure between said distal end of said encasement and said retractor structure, said linkage structure being operable to manipulate the orientation of said distal end of said encasement with respect to said encasement axis.

10. An instrument according to claim 9 wherein said sheath comprises a unitary sheath assembly including a sheath seal constructed and arranged to effect a fluid tight sliding seal between said sheath and said encasement.

11. An instrument according to claim 10 wherein said sheath assembly is disposably removable from said body.

12. An instrument according to claim 10 wherein said sheath assembly is adapted to receive distention fluid near its proximal end and said sheath and said encasement define a fluid conveying passageway for said fluid to the distal end of said sheath.

13. An instrument according to claim 2, further comprising:
an eyepiece, having a longitudinal eyepiece axis, said eyepiece being structurally associated with said body and said proximal end of said bundle; and
coupling structure, connecting said eyepiece to said body, constructed and arranged to permit articulating movement of said eyepiece with respect to said body, whereby to adjust the relative orientations of said body axis and said eyepiece axis.

14. A fiberscopic instrument, comprising:
a handle, having a longitudinal handle axis;
a body, having a longitudinal body axis, a proximal end and a distal end, said body being connected to said handle such that said handle axis is transverse said body axis;
a hollow sheath, having a longitudinal sheath axis, a proximal end and a distal end, said sheath being carried by said body approximately parallel said body axis and including proximal structure coupling said sheath to said body in axial sliding relationship; and
an optics encasement, having a longitudinal encasement axis, a proximal end and a distal end, said encasement extending through said sheath and containing a fiber optic bundle, said bundle having a proximal end and a distal end and being oriented within said body approximately parallel said body axis with the distal end of said bundle extending past the distal end of said encasement;
said sheath being moveable between a distal position in which said encasement is substantially within said sheath and a proximal position in which a distal portion of said encasement projects beyond said distal end of said sheath.

15. An instrument according to claim 14, including:
adapting structure associated with said proximal end of said bundle, constructed and arranged to interface said proximal end of said bundle to an eyepiece; and
an eyepiece, having a longitudinal eyepiece axis, said eyepiece being structurally associated with said body and said adapting structure.

16. An instrument according to claim 15, wherein said adapting structure comprises:
coupling structure, connecting said eyepiece to said body, constructed and arranged to permit travel of said eyepiece with respect to said body, whereby to adjust the relative orientations of said body axis and said eyepiece axis.

17. An instrument according to claim 16, wherein said coupling structure includes a pivot joint between said body and said eyepiece.

18. An instrument according to claim 14 wherein the distal portion of said encasement is flexible and including:
retractor structure mechanically associated with said body, constructed and arranged for manual manipulation between first and second positions;
mechanical linkage structure between said distal end of said encasement and said retractor structure, said linkage structure being operable to manipulate the orientation of said distal end of said encasement with respect to said sheath axis in correspondence to movement of said retractor structure between said first and second positions, respectively, whereby to alter the line of sight of said bundle.

19. An instrument according to claim 18 wherein said retractor structure is constructed and arranged to urge said sheath between said distal and said proximal positions, respectively.

20. An instrument according to claim 19 wherein said retractor and linkage structures are cooperatively constructed and arranged so that said linkage structure is operable in response to movement of said retractor structure between said first and second positions only when said retractor is in its proximal position.

21. A fiberscopic instrument, comprising:
a body, having a longitudinal body axis, a proximal end and a distal end;
a fiber optic bundle, having a proximal end and a distal end, said bundle being housed within said body approximately parallel said body axis with the distal end of said bundle extending past the distal end of said body;
an eyepiece, having a longitudinal eyepiece axis, said eyepiece being structurally associated with said body and said proximal end of said bundle; and
coupling structure, connecting said eyepiece to said body, constructed and arranged to permit pivoting movement of said eyepiece with respect to said body, whereby to adjust the relative orientations of said body axis and said eyepiece axis.

22. A fiberscopic instrument, comprising:
a body, having a longitudinal body axis, a proximal end and a distal end;
a hollow sheath, having a longitudinal sheath axis, a proximal end and a distal end, said sheath being carried by said body approximately parallel said body axis, the distal end of said sheath extending beyond said distal end of said body;
a fiber optic bundle, having a proximal end and a distal end, said bundle being housed within said sheath approximately parallel said body axis with the distal end of said bundle being movable axially with respect to the distal end of said sheath;
adapting structure associated with said proximal end of said bundle, constructed and arranged to interface said proximal end of said bundle to an eyepiece; and
retractor structure mechanically associated with said body, constructed and arranged for manual manipulation selectively to advance or retract said distal end of said sheath with respect to said distal end of said bundle.

* * * * *